(12) United States Patent
Weaver et al.

(10) Patent No.: US 10,960,151 B2
(45) Date of Patent: Mar. 30, 2021

(54) INHALATION DEVICE WITH SHAPE MEMORY ALLOY ACTUATOR

(71) Applicant: Lafayette College, Easton, PA (US)

(72) Inventors: Leslie Ann Weaver, Hatboro, PA (US); Brent Allen Utter, Easton, PA (US)

(73) Assignee: Lafayette College, Easton, PA (US)

( * ) Notice: Subject to any disclaimer, the term of this patent is extended or adjusted under 35 U.S.C. 154(b) by 313 days.

(21) Appl. No.: 15/963,682

(22) Filed: Apr. 26, 2018

(65) Prior Publication Data

US 2018/0311449 A1 Nov. 1, 2018

Related U.S. Application Data

(60) Provisional application No. 62/491,831, filed on Apr. 28, 2017, provisional application No. 62/490,429, filed on Apr. 26, 2017.

(51) Int. Cl.
*A61M 15/00* (2006.01)
*A61M 16/00* (2006.01)

(52) U.S. Cl.
CPC .... *A61M 15/0021* (2014.02); *A61M 16/0003* (2014.02); *A61M 15/009* (2013.01); *A61M 15/0065* (2013.01); *A61M 15/0091* (2013.01); *A61M 2016/0027* (2013.01); *A61M 2016/0039* (2013.01); *A61M 2205/0266* (2013.01); *A61M 2205/18* (2013.01); *A61M 2205/50* (2013.01); *A61M 2205/583* (2013.01); *A61M 2205/8206* (2013.01)

(58) Field of Classification Search
None
See application file for complete search history.

(56) References Cited

U.S. PATENT DOCUMENTS

| | | | |
|---|---|---|---|
| 7,168,597 B1* | 1/2007 | Jones | A61P 9/10 222/402.2 |
| 2002/0189612 A1* | 12/2002 | Rand | A61M 15/0065 128/200.23 |
| 2004/0231667 A1* | 11/2004 | Horton | A61M 15/0065 128/202.13 |
| 2005/0022806 A1* | 2/2005 | Beaumont | A61M 15/009 128/200.14 |
| 2005/0076904 A1* | 4/2005 | Jones | A61M 15/008 128/200.23 |
| 2006/0137681 A1* | 6/2006 | Von Hollen | A61M 15/0091 128/200.14 |
| 2009/0050142 A1* | 2/2009 | Hamano | A61M 15/0096 128/200.23 |
| 2009/0139520 A1* | 6/2009 | Weaver | A61M 11/001 128/203.12 |

(Continued)

*Primary Examiner* — Kathryn E Ditmer
(74) *Attorney, Agent, or Firm* — Vos-IP, LLC (57) ABSTRACT

An inhalation device comprising a housing, a sensor, a microcontroller, and an actuating device controlled by the microcontroller; the housing comprises a mouthpiece having an opening connected to a passage in said housing, wherein the other end of the passage provides an opening for a cartridge; said sensor being in communication with the microprocessor and configured to detect a parameter based on an action to the mouthpiece, and wherein a parameter being reached, the microcontroller engages the actuating device which engages the cartridge to deliver medication through the passage and out of the mouthpiece.

18 Claims, 9 Drawing Sheets

(56) References Cited

U.S. PATENT DOCUMENTS

2012/0298106 A1* 11/2012 Kjellgren .......... A61M 15/0043
128/203.15
2014/0116426 A1* 5/2014 Mullinger ......... A61M 15/0071
128/200.14
2019/0001085 A1* 1/2019 Cottenden ........... A61M 15/009

* cited by examiner

INHALATION DEVICE WITH SHAPE MEMORY ALLOY ACTUATOR

PRIORITY CLAIM

This application claims priority to U.S. Provisional Patent Application No. 62/490,429 filed Apr. 26, 2017 and U.S. Provisional Patent Application No. 62/491,831 filed Apr. 28, 2017, which are herein incorporated by reference in their entirety.

FIELD OF INVENTION

The present application is related to devices for automating or improving the effectiveness of administering inhalation medications through an inhaler, and methods of use and of administering said compounds through a device.

BACKGROUND OF INVENTION

The use of inhaled medications, specifically through compressed gas inhalation devices, is prevalent in asthma and chronic obstructive pulmonary disease (COPD) patients. These inhalers offer the advantage of targeted delivery of a therapeutic to the site of action, typically the airways. These include rescue inhalers such as pressurized metered dose inhalers (MDIs), breath-activated inhalers using dry power and pressurized metered doses, inhalers with spacer devices, and nebulizers.

We are particularly interested in the MDI type devices, and the similar breath-activated devices, that are so commonly used and prescribed to patients in asthma and COPD patients. These devices frequently contain one or more therapeutics, usually including a corticosteroid or other anti-inflammatory drug or a bronchodilator. These classes of compounds are given for maintenance of airway dilation and also for "rescue" type use, where airway diameter is challenged due to an asthma attack, as one example.

While the devices appear to be simple to utilize, studies have shown that the vast majority of patients who use these devices do not use them properly. This results in several issues, namely the requirement for more frequent use of an inhaler, due to receiving insufficient doses of therapeutics, insufficient treatment that leads to secondary disease or progression of disease, hospitalization due to complications from COPD or asthma, where a properly used device could have prevented the complication, among other issues. Indeed, the body of research supports that improper uses include failure to remove the cap, not shaking the inhaler before use, not exhaling before attempting to inhale, insufficient inhalation, miscoordinating the timing of inhalation breath and dispersion of medication, inhaling too rapidly or too shallow, not depressing the inhaler cartridge and inhaling through the nose instead of the mouth.

Costs from secondary disease, progression of disease, unnecessary hospitalizations, excess medication costs and complications lead to an excess expenditure of billions of dollars a year, worldwide. Furthermore, the unnecessary hospitals stays take up valuable time and resources from medical practitioners as well as from those suffering from these diseases.

Certain advances in metered-dose inhaler technologies have created automatic delivery devices that are advanced by a solenoid valve, as one example. However, these existing devices require specialized cartridges for medication dosing, they are larger than typical inhaler, and they lack features to easily allow for manual override of the electronic systems.

SUMMARY OF INVENTION

The present invention is directed to an inhalation device comprising a housing, a sensor, a microcontroller, and an actuating device controlled by the microcontroller; the housing comprises a mouthpiece having an opening connected to a passage in said housing, wherein the other end of the passage provides an opening for a cartridge; said sensor being in communication with the microcontroller and configured to detect a parameter based on an action to the mouthpiece, and wherein a parameter being reached, the microcontroller engages the actuating device which engages the cartridge to deliver medication through the passage and out of the mouthpiece.

In certain embodiments, the sensor is a pressure sensor. The pressure sensor can detect a drop, indicating inhalation, or an increase, indicating exhalation, in pressure within the passage. In certain embodiments, the pressure sensor detects a difference relative to atmospheric pressure of about 0.05 PSI.

In certain embodiments, the actuating device is a shape memory alloy actuator. In other embodiments, the actuation device is selected from the group consisting of a solenoid, a piezoelectric motor, a servo, or other electromechanical actuator.

In certain embodiments, the device comprises an alarm to notify of the sensor being activated. In certain embodiments, the device comprises a further alarm to notify when the sensor is not activated. In certain embodiments, the alarm is audio. In certain embodiments, the alarm is a visual alarm.

The inhalation device may further comprise an activation switch. In certain embodiments, the activation switch must be depressed to energize the system for administration of the medication.

In preferred embodiments an inhalation device comprising a housing, a sensor, a microcontroller, and shape memory alloy actuator controlled by the microcontroller; the housing comprises a mouthpiece having a first opening connected to a first passage in said housing, and a second passage within said housing comprising a second opening configured to receive a pressurized cartridge; within said first passage, a sensor having a first port and a second port, wherein said first port in communication with the first opening and said second port in communication with ambient air; said sensor further configured to a microprocessor and configured to detect a parameter, and wherein a parameter being reached, the microcontroller engages the shape memory alloy actuator, and engages the cartridge to deliver medication through the first passage and out of the mouthpiece. In preferred embodiments, the sensor is a pressure sensor, wherein the pressure sensor is a differential pressure sensor, measuring a difference between the pressure from the first port and the second port. Accordingly, the sensor can detect a drop in pressure within the passage, or simply the difference between the ambient pressure and pressure in the passage connected to the mouthpiece. Preferably the pressure sensor detects a difference relative to atmospheric pressure of at least 0.01 PSI, at least 0.025 PSI, or about 0.05 PSI, including all ranges in between, whether specified or not.

In preferred embodiments, the shape memory alloy actuator is a single wire, being connected to opposing sides of the housing, with a portion of the wire contacting a movable cap. The movable cap having a recess or slot or path for accepting the wire on one side, and contacting the canister and housing on the opposing side; wherein the cap can slide along a portion of the housing. The inhalation device of claim 5, further comprising three bearings connected to each of a left and right side of the housing, wherein the shape memory alloy wire is routed around the three bearings to form at least a first and a second loop in the shape memory alloy wire on each of the left and right sides.

In preferred embodiments, the inhalation device further comprising at least one guide post on each of the left and right sides of the housing, wherein said guide posts comprise at least one opening of sufficient diameter to thread the shape memory alloy wire through said at least one opening and orient said shape memory alloy wire around each of the three bearings to orient the first and second loops on each of the left and right sides. Preferably, wherein the shape memory alloy wire has a diameter of about 0.015 inches. Preferably, the shape memory allow wire actuator provides an actuation distance of at least 0.055 inches of travel when actuated.

In a preferred embodiment, the inhalation device further comprising an indicator to indicate the activation of the actuator, for example, wherein the indicator is an audio or visual alarm. In certain embodiments, the device further comprising an activation switch. In certain embodiments or methods, the activation switch must be depressed or engaged to energize the system for administration of the medication.

In certain embodiments, the inhalation device comprises a wireless transmitter.

A method of automatically administering a medication from a cartridge comprising said medication under pressure comprising: inhaling into an automatic inhalation device, said automatic inhalation device comprising a housing, a sensor, a microcontroller, and shape memory alloy actuator controlled by the microcontroller; the housing comprises a mouthpiece having a first opening connected to a first passage in said housing, and a second passage within said housing comprising a second opening configured to receive a pressurized cartridge; within said first passage, a sensor having a first port and a second port, wherein said first port in communication with the first opening and said second port in communication with ambient air; breathing into said mouthpiece at sufficient duration and air flow to generate a negative pressure at the first port, sufficient to differentiate said pressure from the second port; activating the microprocessor to heat the shape memory alloy, wherein the heat shrinks the shape memory alloy from a first length to a second length; the shortening length pressing on a cap, said cap in contact with said cartridge, and said pressure forcing a valve stem on the cartridge against a valve post, thereby depressing said valve stem a releasing said medication under pressure.

An inhalation device comprising a housing having a left and right side, a sensor, a microcontroller, a housing cap, and shape memory alloy actuator controlled by the microcontroller; the housing comprises a mouthpiece having a first opening connected to a first passage in said housing, and a second passage within said housing comprising a second opening configured to receive a pressurized cartridge within said second passage, and a valve post, connected to the first and second passages, defined to receive and contact a valve stem from a pressurized cartridge; said left and right sides of the housing each having at least three bearings, positioned to allow for the shape memory alloy actuator to create at least a first loop on each of the left and right sides, sufficient to extend the length of the shape memory alloy actuator, with a portion of the shape memory alloy actuator passing over the cap; within said first passage, a sensor having a first port and a second port, wherein said first port in communication with the first opening and said second port in communication with ambient air; said sensor further configured to a microprocessor and configured to detect a reduction in pressure, and wherein a reduction in pressure is reached, the microcontroller engages the shape memory alloy actuator, and engages the cap, which compresses the cartridge to deliver medication through the first passage and out of the mouthpiece.

In preferred embodiments, said shape memory alloy actuator has a length between 12 and 15 inches, a diameter of 0.015 inches, and, wherein heating of the shape memory alloy actuator to its phase change temperature, results in an actuation of at least 0.055 inches.

In preferred embodiments, the Shape memory alloy actuator has a phase change temperature of about 70 C. Accordingly, at such temperature, it is necessary to coat said shape memory alloy with a coating to prevent damage to the housing.

DETAILED DESCRIPTION OF THE EMBODIMENTS

Inhalation devices, including ubiquitous inhalers, comprise a housing and a pressurized medication canister. The housing comprises a mouthpiece and an opening for receiving the pressurized medication canister. The inhaler works by pressing down on the pressurized medication canister, which activates the canister to release a quantity of compressed gas and medication. These are then inhaled by the user who places their mouth on the mouthpiece.

While this seems simple in principle, in practice, actually inhaling and taking all of the dosed medication is difficult. Therefore, patients end up either receiving insufficient medication, or require multiple pumps on the canister, all of which leads to administration of an unknown amount of medication.

Figure 1A:
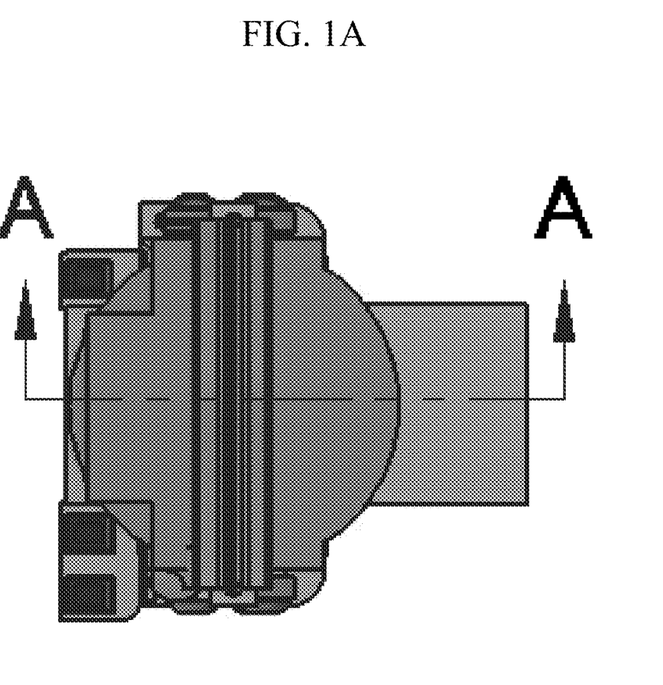
FIGS. 1A, 1B, and 1C depict an embodiment of an inhalation device, (A) depicting a top plan view; (B) depicts a cross-sectional view through A-A; and (C) details the encircled portion for greater scale of 1B.
Figure 1B:
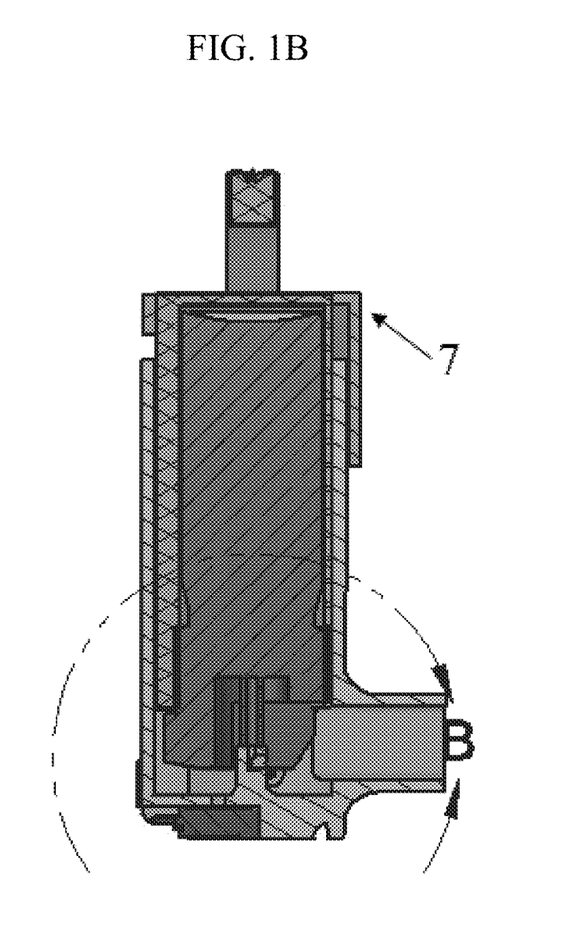
Figure 1C:
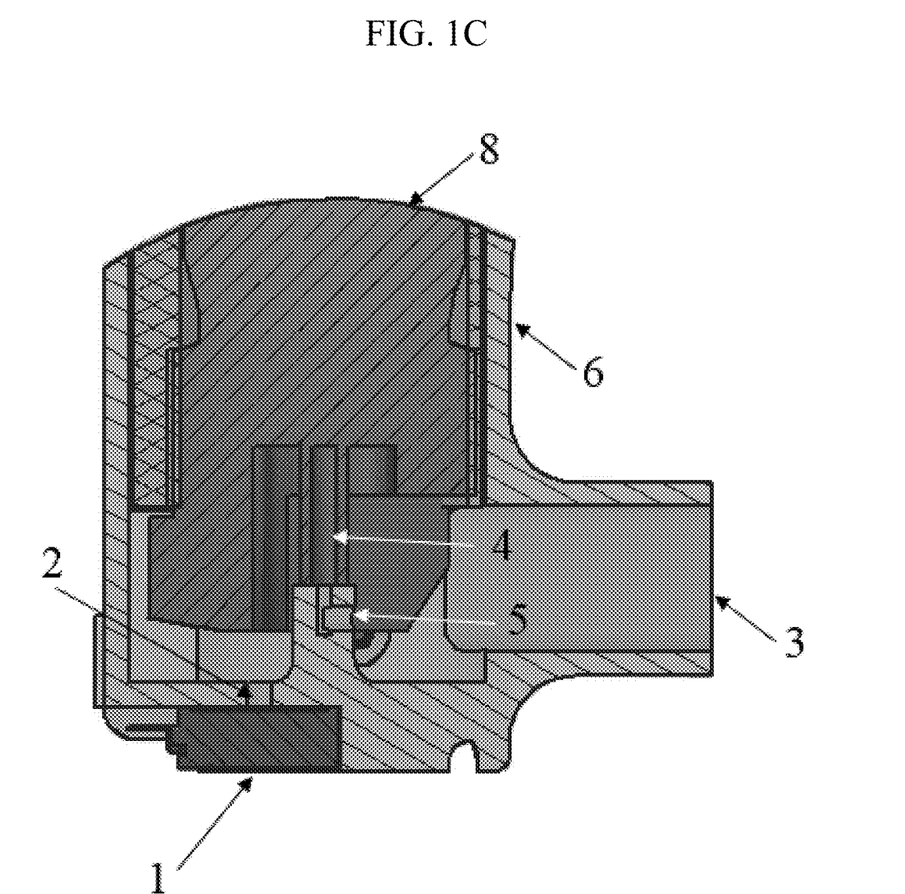

Accordingly, a new device is proposed herein, that will reduce these issues. An automated inhaler, as depicted in FIG. 1, comprises an inhaler housing 6, and an inhaler cap 7. The inhaler comprises an actuator that applies a compressive force on the inhaler cap 7 when triggered by a microcontroller that is interfaced with a pressure sensor 1. The pressure sensor 1 measures the pressure within the vent 2 connecting the pressure sensor 1 to the inside of the housing 6. A valve post 5 is actuated by the actuator and depresses the valve stem 4 on a medicine cartridge 8. The housing can be shaped like an ordinary inhaler device, having a mouthpiece on one end, and an opening with a second passage on the other end for receiving the medicine cartridge. A first passage connects the mouthpiece to a sensor and to the valve stem components, wherein upon compression of the valve stem 4, medication is released from the medicine cartridge 8 and can be inhaled through the passage connected to the mouthpiece. Accordingly, the cap 7 is depicted in FIG. 1A in the top plan view, with the side cross-sectional view of FIG. 1B depicting the cap 7. The detail view of FIG. 1C then depicts the remaining features, including the mouthpiece 3.

The pressure is generated when a patient places their mouth on the mouthpiece 3 within the inhaler housing 6. As the breath is drawn the pressure within the housing decreases and the differential pressure sensor 1 triggers. This causes the SMA actuator of the device to activate and depresses the valve stem 4 release the medication. Indeed, the pressure sensor 1 measures the breath of the patient and indicates that the patient is providing an appropriate breath, which then triggers the microcontroller trigger the actuator.

Figure 2A:
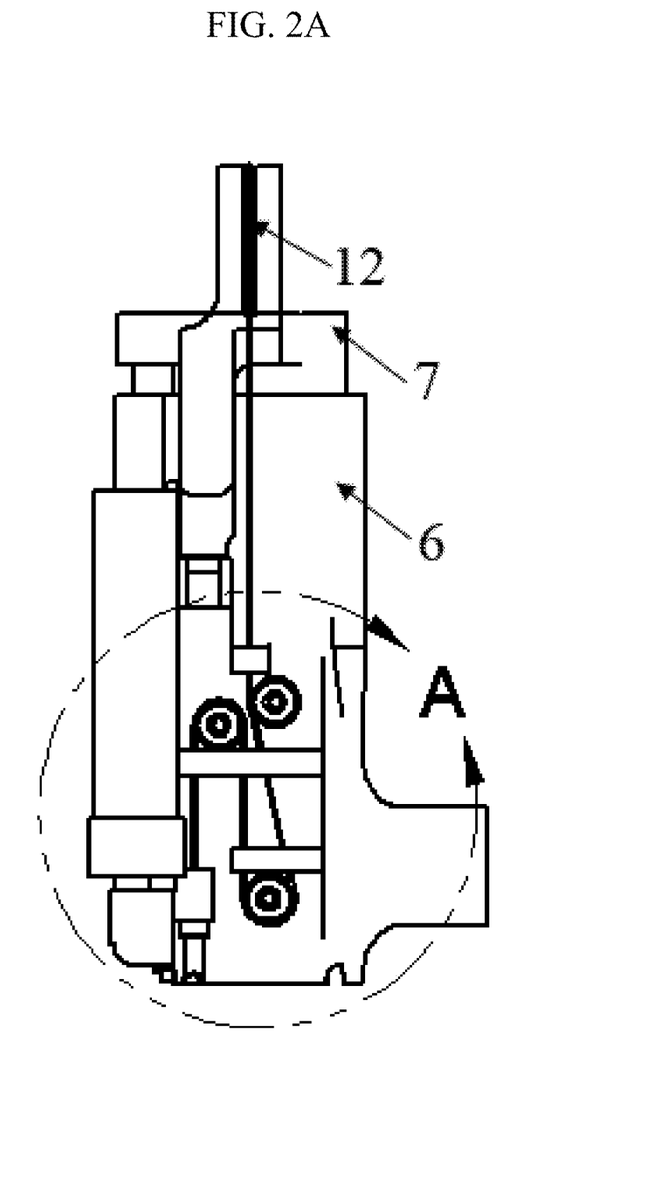
FIGS. 2A and 2B depict a side profile image depicting the SMA actuator and FIG. 2B is an enlarged view of the orientation of the SMA actuator.
Figure 2B:
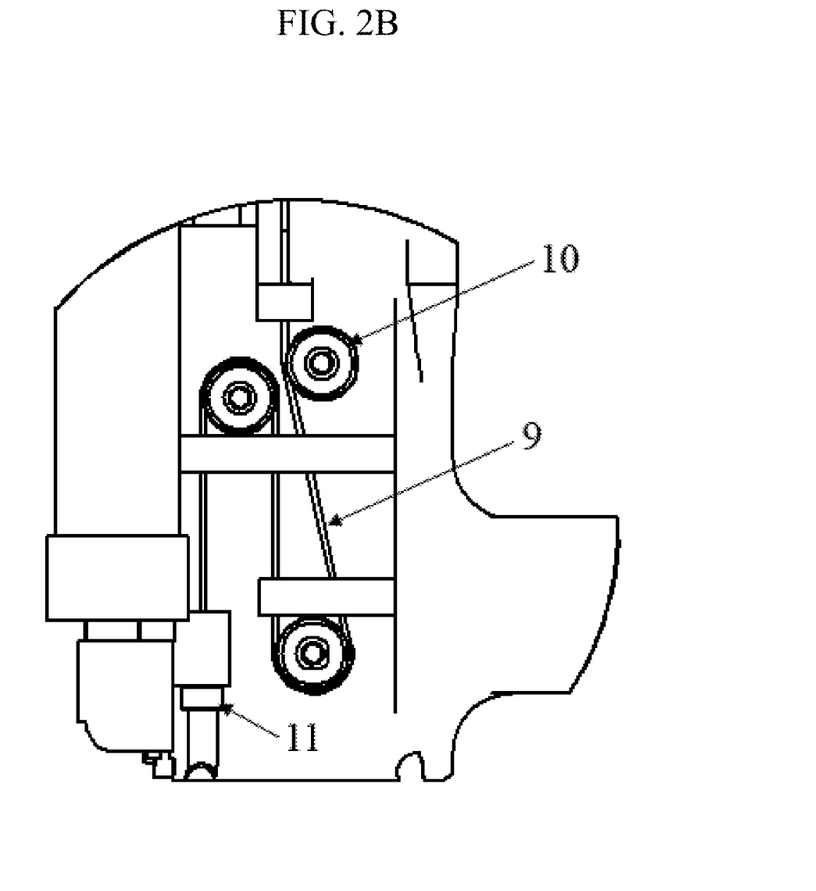

FIG. 2 provides a section view of the automated inhalation device, specifically of the SMA activator. When the user inhales through the mouthpiece 3, the pressure sensor 1 will measure the drop in pressure relative to atmospheric pressure. When a certain threshold is met, or a separate criterion met, the microcontroller will initiate actuation of the inhalation cartridge 8. Thus, instead of the user manually actuating the cartridge 8, as in prior art devices, the automatic activation will ensure that the medication is activated when the patient has properly inhaled to receive the medication to the fullest extent.

While other sensors may be suitable in certain embodiments, the preferred embodiments here, utilize a SMA actuator. The SMA actuator is preferable because it is a compact and lightweight actuator that does not significantly modify existing inhaler design, and does not modify the existing inhalers significantly in cost, size, or weight. Furthermore, the SMA actuator provides sufficient force, on the order of pounds and a stroke on the order of tenths of inches. Furthermore, the SMA wire is amenable to integration with small or handheld devices, because it can be easily routed along confined paths, thus allowing us to conform to the existing form of the inhalation devices.

For example, FIG. 2 depicts a side profile of the inhalation device, comprising a cap 7, a housing 6, an inhalation mouthpiece 3, and a length of SMA wire 9. The SMA wire connects around three roller bearings 10 on each side of the inhalation device. One end of the SMA wire 9 is connected with an anchoring screw 11. This allows the SMA wire to follow a serpentine like path, enabling elongation of the SMA wire, without increasing the size of the inhalation device. Other suitable anchoring elements are usable, including crimping the wire, a nut, a vented bolt, or an appropriate adhesive. The requirement is that the wire must hold under repeated stresses without failure. Accordingly, a crimping device held under an opening for the wire generates a secure fit.

The SMA wire 9 extends from a left side of the housing to a right side of the housing, and crosses above the top of the cap 7 within a path 12, and fits within a recess of path 12 on this top side of the cap 7. The underside of the cap is in contact with the canister 8, and when the SMA wire 9 shortens, due to the activation, the cap 7 is compressed and presses the canister 8 to force the canister valve stem 4 to release medication.

The SMA wire 9 may be coated with an appropriate coating. This is done for two reasons: first, the wire heats up and may cause damage to the inhalation device, if it were touching plastic or metal, and secondly, to prevent burns to the user.

When the SMA wire is triggered by a microcontroller the SMA wire is heated and thus changes length, which in this case, shortens the length of the wire, and thus compresses the cartridge 8 and thus compresses the valve stem 4 to release medicine from the cartridge 8.

Figure 3A:
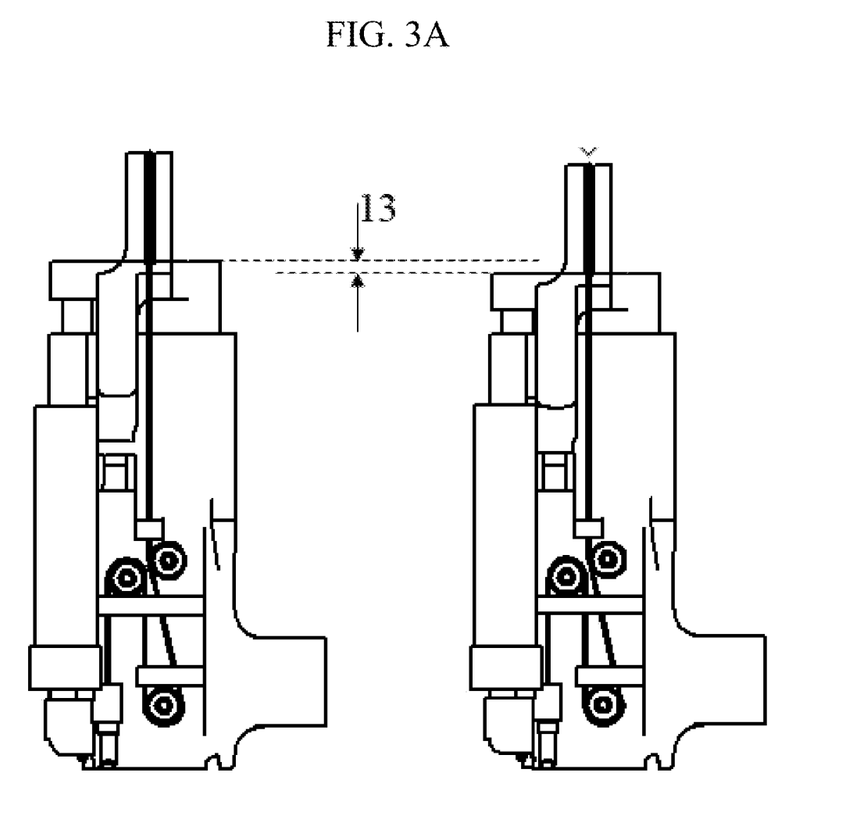
FIGS. 3A and 3B depicts actuation of the inhalation device with 3A showing non-compressed/actuated and FIG. 3B depicting the actuated version that is expelling fluids.
Figure 3B:
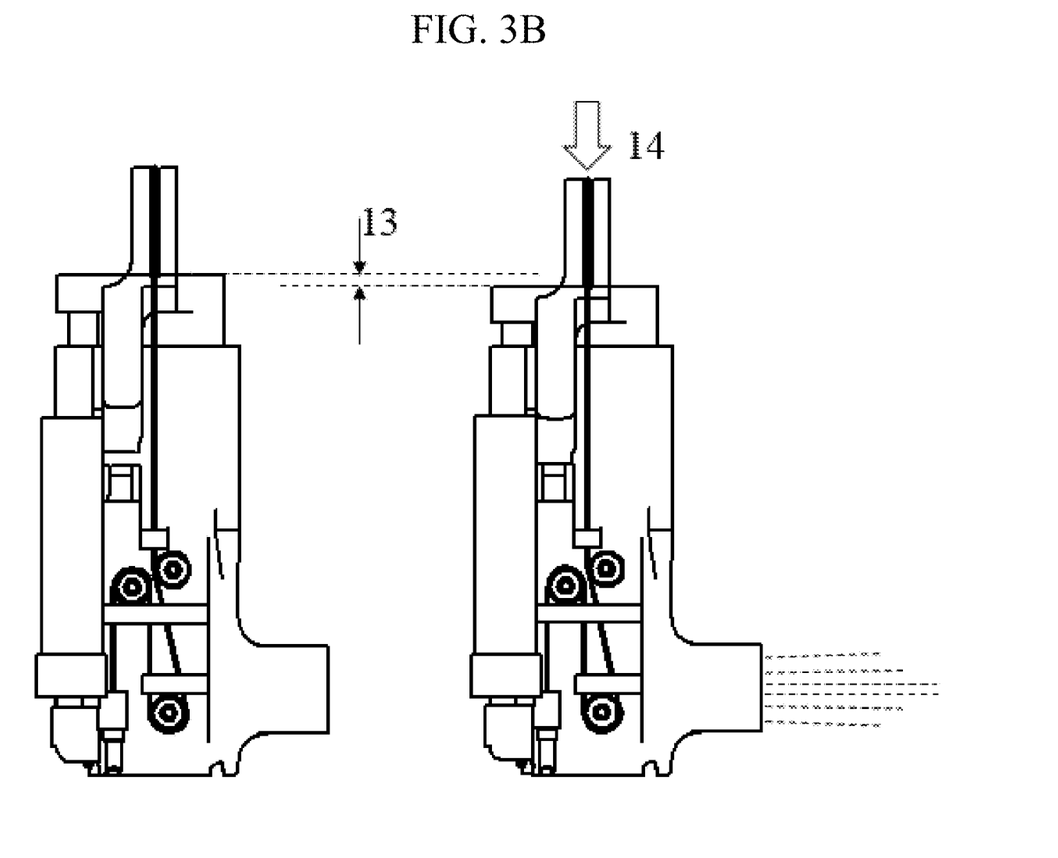

Indeed, FIG. 3 provides a side view of the device in action. FIG. 3A depicts the SMA wire 9 in a first state. As a vacuum is created on the mouthpiece 3, the pressure sensor 1 signals to a microcontroller to send a current through the SMA wire 9. This creates the change in displacement 13, and thus generates a force 14 sufficient to compress the cartridge 8 to expel activate and compress the valve stem 4 and release the medicine. A flow chart of this process and the various feedback loops are provided in FIG. 4.

Figure 4:
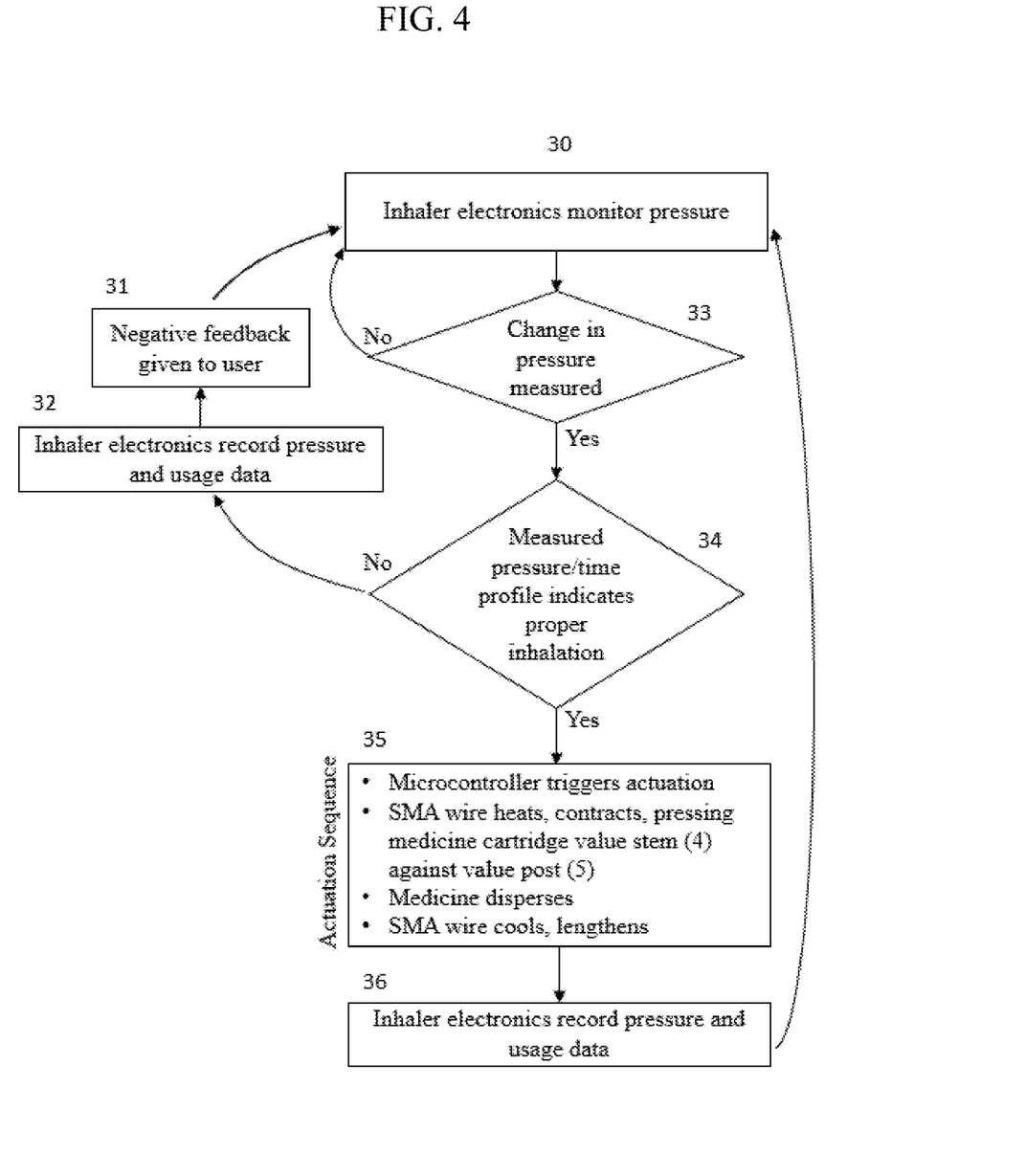
FIG. 4 is a flowchart depicting the operation of the device.

In FIG. 4, a person shakes the inhalation device, this properly mixes the medication in the cartridge 8. After shaking, the mouthpiece cap/cover is removed and the patient exhales and then inhales. The inhalation step creates a differential pressure between the ambient air and the air within the device. The differential pressure sensor 1 takes a measurement of the ambient air (outside of the device) and then air within the vent 2. Upon a proper change in pressure being measured 33, and the measured pressure/time profile indicated proper inhalation 34, then a microcontroller triggers actuation 35. This actuation 35 is generated wherein the SMA wire heats, contracts, and presses the cartridge 8 valve stem 4 against the valve post 5, thus dispersing the medication. The SMA wire then cools, and lengthens, thus releasing the valve stem 4 and is ready for a further actuation, if necessary. The inhaler electronic components record pressure, and usage date 36.

In certain aspects of FIG. 4, proper aspects of the actuation process are not met and thus the next step will not occur. For example, if there is no change in pressure 33 measured, then it cannot proceed to measuring the time for proper inhalation of step 34. In certain examples, if an insufficient pressure is measured, a notification or alarm may be generated. Such information, including the insufficient pressure can be recorded in the electronic system 36. If the user generates either an insufficient pressure change, or does not sustain the pressure change for sufficient duration in 34, then in the inhaler records this data 32, and negative feedback 31 is given to the user. This may be the alarm step. Lack of pressure may occur due to any number of errors such as failure to remove a cap from the mouthpiece, too short of breath, or insufficient breath depth. Each instance typically results in medication failure, and thus, by preventing such actuation in these cases, the patient must perform the inhalation properly to get medication.

In certain embodiments, an audio or visual notification is provided for one or both of a successful use or an unsuccessful use of the inhalation device. The device can include an alarm or visual signal indicating that the criteria was not met so as to indicate to the patient to re-attempt the breath to generate the sufficient criteria. For example, the alarm may make a specific tone when the criteria is successful and a different criteria when unsuccessful. Alternatively, or in combination, a set of lights can indicate status to reach the criteria. One example uses one light for success and another light for fail. A further example uses a set of three lights can indicate. A first light indicating a breath started, a second light, meaning breath more, and the third light indicating the criteria being met.

The pressure sensor 1 is configured to prevent certain user errors, when used with the automated inhalation device. For example, the pressure sensor 1 prevents discoordination, with respect to time, of intake of breath and the release of medication. The pressure sensor can be configured to sense one or more components, including inhalation that is too fast, inhalation that is too deep, inhalation that is too shallow, failure to remove a cap from the mouthpiece (no inhalation to the device), not exhaling before inhaling, intentional lack of use.

Accordingly, the alarm features can indicate or alarm on a daily basis, to prevent the intentional lack of use. Also alarms can identify the remaining issues, through one or more tones, or other audio or visual indications on the device.

The system can include memory within the device, attached to and/or incorporated with the microprocessor to obtain and capture data over time. This allows the device to aggregate data over time, identify trends, track efficiency of use and of the medical treatment, and allows the device to therefore collect and share data with a healthcare provider. For example, after a pre-determined number of failed uses, the healthcare provider can be signaled to provide a follow-up with the patient to refresh or retrain the patient on the proper manner to use the device. Such patient support can be in-person, video, audio, etc. and can be billed to the patient through as if a patient visit, for reimbursement purposes.

In preferred embodiments, the device functions as is generally described in FIG. 4, to utilize the automatic inhaler device. In a simplified embodiment, a user removes the mouthpiece cap from the mouthpiece and inhales. The pressure sensor 1 then measures a drop in pressure and transmits a signal to the microcontroller 17. The microcontroller 17 initiates action of an actuator. The inhaler cartridge 8 is compressed or activated, for example, through compression of the inhaler cap 7. The compression or activation releases the medication from the compressed cartridge with optimal timing, coinciding with the pressure at the sensor. User data are stored and aggregated and feedback is provided to the user.

Figure 5:
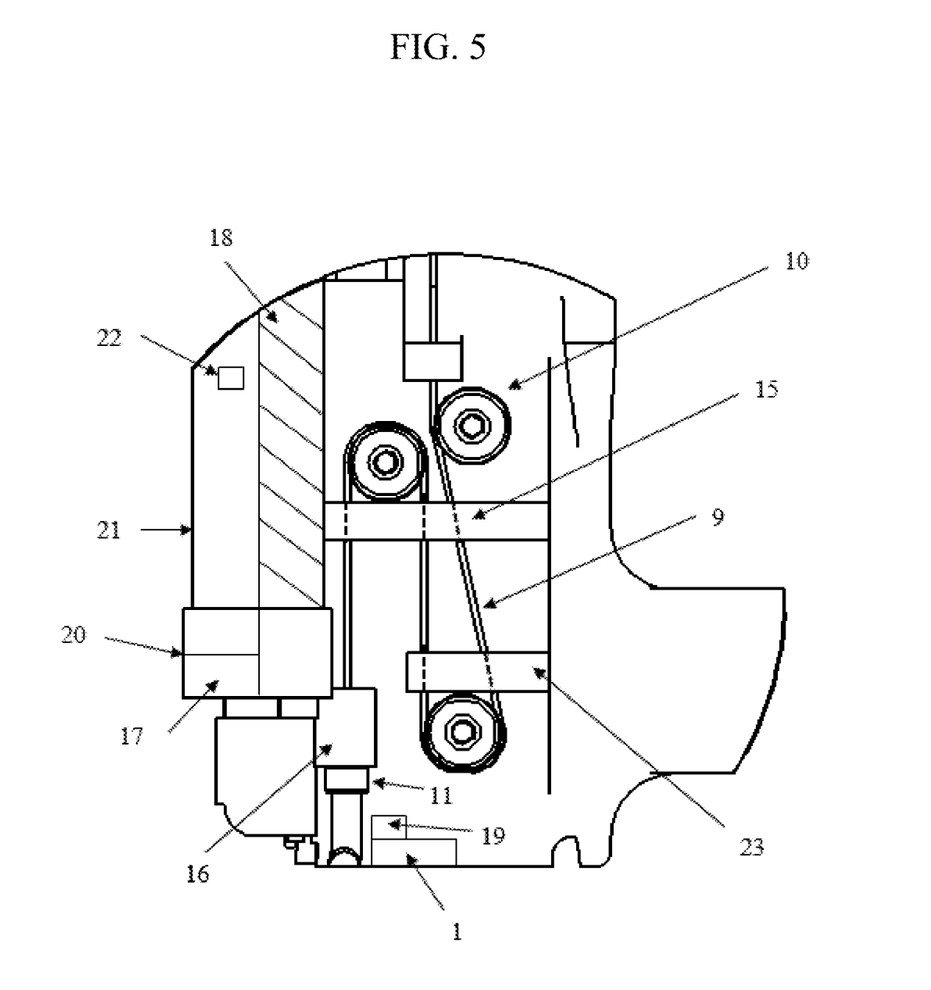
FIG. 5 depicts a detailed view of the inhalation device and certain electrical components.

FIG. 5 provides detail of exemplary placement of some of the various components necessary to run the device. The particular placement and scale of such items is merely for example and does not limit their positioning in the embodiments. It may be possible to place all electronic components on a single board, and to place the batter separate from the board to allow for maximum battery size, while retaining the small form of the device. This is commonly understood by those who manufacture electronic devices. For example, FIG. 5 details that the SMA wire posts 23 having holes in them for routing the SMA wire. The SMA wire is shown going through the SMA wire posts 23, by dotted lines 15. The device further comprises an amplifier 16, suitable for generating a current to heat the SMA wire for actuation. The device further comprises a microcontroller 17 for performing certain tasks, a battery 18 to run the electronic components, a sensor amplifier 19, and memory 20 and other electronics. An optional Wi-Fi/Bluetooth/wireless connectivity component 21 can be included, through a wired port is also suitable at the same position. The device may further comprise an activation switch 22 on the housing. This switch can be turned on/off to stay in one position, like a light switch, a compressed switch, wherein the user compresses the switch to activate the device, or other suitable binary on/off switch. By activation of the switch 22, the device is powered and then following the process in FIG. 4, the medication can be administered to the patient.

Optionally connected to or tethered to the device is a wireless computing device, such as a tablet, phone, or computer that can electronically communicate with the device. This device can access or communicate data from the device into a readable format. For example, data on time and frequency of use, on the pressure recognized at the sensor, time to reach a certain pressure at the sensor, failed attempts, successful attempts, and other data corresponding to use.

As connected to a device, the timing and use can be correlated to actual time of day, weather, pollen counts, and even towards exercise or activity, to identify certain triggers that may be present that require use of the inhalation device.

A benefit of the inhalation device is the automatic application, which removes the uncertainty of correct use. This increases the odds that a patient will receive the appropriate medicated dose, when necessary with the inhalation device. However, as designed, the device retains the mechanical nature, to be used as a pure rescue inhaler.

For example, if the patient is unable to create the necessary pressure to the sensor, the device will not automatically express the medication. However, a patient can then manually depress the compressed cartridge to express the medication. Similarly, if the device fails from battery depletion or other electronic malfunction, the device will still function as an ordinary mechanical inhaler.

This is an important safety issue, and thus the mechanics of the device are such that the mechanical activation is not unnecessarily hindered.

Testing of the SMA Actuator

The device was designed to be a compact, lightweight inhalation device, capable of using off-the-shelf pressurized cartridges for metered dose inhalers. To maintain the proper size, and generate sufficient force, the actuator used for automatic activation must provide forces on the order of pounds of force and a stroke in the order of tenths of inches. Accordingly, we evaluated the use of SMA wire for its ability to meet these limitations, and because it is lightweight, and amenable to routing on the small hand-held device of the inhalation device, thus eliminating the need to create a new device form.

The inhaler housing and cap are intended to fit a standard medicine cartridge and allow for self-replacement of the spent cartridge. An SMA wire is mounted on one side of the housing, passed through three bearings to create two loops in the SMA wire. This allows us to effectively increase the length of the SMA wire and increase its actuation stroke, without having to increase the size of the inhalation device (for example, making it an inch or two taller). As described above and shown in the various figures, a sensor engages with the external environment and also with an internal environment, measuring a pressure differential between these spaces.

The inhalation device is intended to coordinate the timing of the inhalation breath of a patient with the depression of the medicine cartridge. To coordinate the timing, differential pressure sensor monitors the atmospheric pressure and the pressure within the inhaler housing. A breath pulls air within the housing, creating a vacuum and reduces the pressure within the housing to potentially trigger the SMA actuator. Once the sensor 1 detects proper criteria, including rapidity, duration, and consistency of breath, among a list of possible metrics which can be defined by a practitioner for each individual (See FIG. 4), the microcontroller 17 indicates to the amplifier 16 to heat the SMA actuator. The placement of the sensor within the housing ensures that a breath must be being pulled from the mouthpiece and not a nasal breath, thus eliminating one of the primary errors in use of the devices. Once the microcontroller signals to the amplifier to drive current through the SMA wire, the wire increases in temperature via Joule heating, and induces the transformation from Martensite to Austenite. As this transformation occurs, the inhaler cap 7 is drawn toward the inhaler housing and compresses the cartridge valve stem to release medicine through the mouthpiece. Ideally, the patient continues to inhale and the medication is passed into the lungs. The SMA wire is them allowed to transform from Austenite to Martensite after a time elapses (or a limit switch) measures that the cartridge has been sufficient depressed. As the SMA wire cools, the wire lengthens and the pressure imparted by the cap is released and thus the device is re-set.

The design of the SMA wire actuator, where the SMA wire is used under pure tension requires a determination of wire diameter and length given a desired stroke against a non-constant external load that must be measured or predicted. To test these parameters, the SMA wire is mounted that it acts as two wires in parallel to prevent the inhaler cap from binding against the inhaler housing, when strain is recovered. A parallel actuator configuration reduces the minimum required wire diameter to prevent the wire stress from exceeding the maximum allowable magnitude.

To characterize the external load, load and displacement data were collected for several loading and unloading cycles. The cartridge was rigidly mounted to a carriage of a linear stage and linear encoder strip was used to measure displacement. A bolt on the carriage was manually rotated to drive the stage, until the depression required was indicated by the release of the aerosolized medicine. This distance was measured at approximately 0.09 inches. However, the valve did not need to be retraced the entire 0.09 inches to re-set the system, instead, we calculated that only a length of 0.055 inches was necessary for re-setting. As the cartridge was depressed, the load was approximately 5.5 lbf (load) at 0.025 inches and rose to approximately 7.5 lbf at 0.09 inches.

Accordingly, a wire meeting these limitations was selected based on minimum diameter. Here, because the SMA wire is acting in parallel, being attached on each side in equivalent orientation, the maximum external load was measured to be about 7.5 lbf, and based on our review, the minimum commercially available wire was determined to be 0.015 inches. A wire from Dynalloy, Inc. defined such a wire with a 172 MPA maximum allowable stress. A low temperature (70 C) composition was elected to reduce the power required to heat the wire above its transition temperature and activate the wire.

Data was collected using a 0.015 inch diameter wire (not shown). Data was collected by completely transforming the wire to Austenite via Joule heating against an initial external load; two, recording the length of the wire and the magnitude of the externally applied constant weight, three, allowing the wire to cool, four, recording the measurements again, five, completely transforming the SMA wire from Austenite via Joule heating again, six, increasing the magnitude of the externally applied weight, and seven, repeating steps two-six again until the maximum allowable wire stress was reached. To transform this data into stress-strain space, the Austenite free length of the wire was found by applying wire lengths to strains. The stress of the wire was found by dividing the externally applied loads by the cross-sectional area of the SMA wire.

Accordingly, to evaluate the design space used to predict the stroke of the actuator the following steps were taken: determining where the external load curve intersects the Austenite curve while the wire is transforming the Austenite (point A), and determining where the external load curve intersects the Martensite curve while the wire is transforming the Martensite (Point B). Points A and B are equilibria and their difference represents the total actuation strain, which was predicted to be approximately 0.008.

A straight SMA wire mounted to the inhaler would have an Austenite free length of approximately 8.8 inches, assuming the wire was mounted while at its Austenite free length with the inhaler cartridge depressed. When the load and displacement behavior of the inhaler cartridge was mapped into the stress-strain space of this shorter wire, a greater total actuation stroke of 0.011 was found. Thus, the actual stroke provided would be approximately 0.011×4.4 inches (because of the parallel configuration of the SMA wire) and thus equaling only 0.049 inches. This is less than the 0.055 inches needed to reset the inhaler cartridge for subsequent use.

Lengthening the wire would require extending the length of the device by nearly one inch. This was untenable, as it would alter the form understood and used by millions who use inhalers. Accordingly, an alternative, and as depicted in the Figures, was to route the SMA wire along three bearings to create two loops in the wire on each side of the device, and lengthening the SMA wire by 4.4 inches. This length was sufficient to achieve the desired stroke length. Precise orientation of the wires could allow for additional loops on each side, thus further lengthening the SMA wire, should different cartridges have a need for a larger stroke length.

As detailed in the figures, the SMA wire is mounted on each side of the housing, and the wire crosses over the top of the cap 7. To increase the length of the SMA wire, the wire is guided along a serpentine path using bearings as loop points. The wire, as depicted in FIG. 5 passes through certain SMA routing posts 23 to keep the SMA wire within this path and prevent it from sliding off the bearings. The wire is covered with a high temperature coating, for example PEEK tubing, which prevents the heated wire from contacting and melting the housing or burning the user. The total length of the SMA wire, when routed using two loops on each side of the housing is approximately 13.5 inches. Each loop adds approximately one inch to the length. A single loop could be used, but would require the anchor being repositioned. A third, or more loops could also be used, though both space and weight become potential issues.

The pressure sensor 1 we tested was a +/−15 PSI differential pressure sensor, mounted to having one port communitive with the air outside of the inhaler and one port within the air inside of the housing. When the sensor is positioned on the bottom of the housing, the exterior port is positioned simply to be in communication with the air outside of the mouthpiece. This way the interior port only accesses pressure/air from within the mouthpiece opening or passage. The output of the sensor is amplified by a gain of approximately 640, with an instrumentation amplifier (INA125, Burr Brown) and digitized by a 10-bit ADC on a microcontroller. Additionally, a Hall Effect sensor (SS49D, Honeywell) and permanent magnet pair may be mounted to measure the displacement of the inhaler cap relative to the housing.

The functionality of the device was confirmed using a 60 mL syringe to draw air from the mouthpiece, mimicking an inhalation breath. Before, during, and after the inhalation breath was mimicked, the microcontroller recorded the displacement of the inhaler cap and the measured pressure. A simple criterion was set for the microcontroller to actuate the SMA wire: if the measured pressure equals −0.033 PSI or less for one measurement, trigger the SMA wire to actuate. Duration of the actuation was set to 1.25 seconds, during which a current of approximately 2.65 amps was applied to the wire and the inhaler cap displaced 0.072 inches. The minimum cartridge valve reset displacement of 0.055 inches was achieved approximately six seconds after the SMA wire started cooling, and the position of the inhaler cap was restored after approximately 18 seconds after the SMA wire was allowed to cool. Despite the length of SMA wire used, the actuation stroke was greatly reduced by the stiffness of the external system and its hysteretic load-displacement behavior. However, the measured inhaler cap displacement of 0.072 inches sufficiently exceeded the 0.055 inch prediction by 0.017 or about 31 percent.

Heating of the SMA was provided by a DC power supply at approximately 9 volts. Accordingly, to power the wire on the working device, a battery having a 9 volt value may be utilized. For example rechargeable NiMH, LiPo, or other similar high capacity batteries are suitable for use. For example a 200 MaH battery would provide sufficient charge, under typical use, to meet all of the metered doses in a usual canister. Other sized batteries are known to those of ordinary skill in the art. Replacement or charging of a batter can be performed by means known to those of ordinary skill in the art.

Accordingly, the device can be used in appropriate methods for administering pressurized medications from a compressed canister comprising: shaking the inhalation device; removing a mouthpiece cover; exhaling a breath; inhaling through the mouthpiece; triggering the pressure sensor; activating an SMA wire actuator; compressing the canister against the housing of the inhalation device; using a microcontroller, recording the pressure and actuation of the device. In certain embodiments, the exhaling a breath is performed by first exhaling into the mouthpiece, wherein the pressure sensor records an increase in pressure before the exhalation step. Wherein when the increase in pressure is required to activate the SMA wire actuator.

In certain instances, the battery fails, a patient is unable to trigger the actuator, or the device fails to simply properly function. The inhalation device as depicted and described herein, simply contains a cap 7 over the canister 8, and thus manual activation of the compressed canister 8 can be easily performed, if needed. Thus, in an emergency, manual use can be performed without modification of the device. Furthermore, this manual application can be recorded by the microprocessor and annotated in the data collected. Such information can then be accessed by a medical practitioner to give information about the patient's use, typical use, and allow for training for proper use or replacement, as necessary.

What is claimed is:

1. An inhalation device comprising a housing, a sensor, a microcontroller, and a shape memory alloy actuator configured to be controlled by the microcontroller, wherein the shape memory alloy actuator is a single wire connected to opposing sides of the housing and a portion of the wire contacting a movable cap; the housing comprises three bearings connected to each of a left and right side of the housing, wherein the shape memory alloy wire is routed around the three bearings on each of the left and right sides to form at least a first and a second loop in the shape memory alloy wire on each of the left and right sides, and the housing further comprising a mouthpiece having a first opening connected to a first passage in said housing, and a second passage within said housing comprising a second opening configured to receive a pressurized cartridge; said sensor having a first port and a second port, wherein said first port is in communication with the first opening and said second port is in communication with ambient air; said sensor further connected to said microcontroller and configured to detect a parameter, and wherein upon said parameter being reached, the microcontroller is configured to engage the shape memory alloy actuator and the movable cap and is configured to engage the cartridge to deliver medication through the first passage and out of the mouthpiece.

2. The inhalation device of claim 1, wherein the sensor is a pressure sensor.

3. The inhalation device of claim 2, wherein the pressure sensor is a differential pressure sensor for measuring a difference between pressure from the first port and pressure from the second port.

4. The inhalation device of claim 2, wherein the sensor is configured to detect a drop in pressure within the first passage.

5. The inhalation device of claim 3, wherein the pressure sensor is configured to detect a difference relative to atmospheric pressure of at least 0.01 PSI in order to deliver the medication.

6. The inhalation device of claim 3, wherein the pressure sensor is configured to detect a difference relative to atmospheric pressure of at least 0.025 PSI in order to deliver the medication.

7. The inhalation device of claim 3, wherein the pressure sensor is configured to detect a difference relative to atmospheric pressure of about 0.05 PSI in order to deliver the medication.

8. The inhalation device of claim 1, further comprising an indicator to indicate the engagement of the shape memory alloy actuator.

9. The inhalation device of claim 8, wherein the indicator is an audio or visual alarm.

10. The inhalation device of claim 1, further comprising an activation switch.

11. The inhalation device of claim 10, wherein the activation switch is configured to be depressed to energize the microcontroller for administration of the medication.

12. The inhalation device of claim 1, further comprising a wireless transmitter.

13. The inhalation device of claim 1, further comprising at least one guide post on each of the left and right sides, wherein said guide posts each comprise at least one opening of sufficient diameter to thread the shape memory alloy wire through said at least one opening and orient said shape memory alloy wire around each of the three bearings to orient the first and second loops on each of the left and right sides.

14. The inhalation device of claim 13, wherein the shape memory alloy wire has a diameter of about 0.015 inches.

15. The inhalation device of claim 13, wherein the shape memory alloy wire actuator provides an actuation distance of at least 0.055 inches of travel when actuated.

16. A method of automatically administering a medication from a cartridge comprising said medication under pressure comprising: inhaling into an automatic inhalation device, said automatic inhalation device comprising a housing, a sensor, a microcontroller, and a shape memory alloy actuator controlled by the microcontroller, wherein the shape memory alloy actuator is a single wire connected to opposing sides of the housing and a portion of the wire contacting a movable cap; the housing comprising three bearings connected to each of a left and right side of the housing, wherein the shape memory alloy wire is routed around the three bearings on each of the left and right sides to form at least a first and a second loop in the shape memory alloy wire on each of the left and right sides, and the housing further comprising a mouthpiece having a first opening connected to a first passage in said housing, and a second passage within said housing comprising a second opening configured to receive a pressurized cartridge; said sensor having a first port and a second port, wherein said first port is in communication with the first opening and said second port is in communication with ambient air; inhaling through said mouthpiece at sufficient duration and air flow to generate a negative pressure at the first port sufficient to differentiate said pressure from the second port; activating the microcontroller to heat the shape memory alloy, wherein the heat shortens the shape memory alloy from a first length to a second length; the shortening length pressing on the movable cap, said movable cap in contact with said cartridge, and said pressing forcing a valve stem on the cartridge against a valve post, thereby depressing said valve stem and releasing said medication under pressure.

17. An inhalation device comprising a housing having a left and right side, a sensor, a microcontroller, a housing cap, and a shape memory alloy actuator configured to be controlled by the microcontroller; the housing comprising a mouthpiece having a first opening connected to a first passage in said housing, and a second passage within said housing comprising a second opening configured to receive a pressurized cartridge within said second passage, and a valve post, connected to the first and second passages, defined to receive and contact a valve stem from the pressurized cartridge; said left and right sides of the housing each having at least three bearings, positioned to allow for the shape memory alloy actuator to create at least a first loop on each of the left and right sides sufficient to extend the length of the shape memory alloy actuator, with a portion of the shape memory alloy actuator passing over the housing cap; said sensor having a first port and a second port, wherein said first port is in communication with the first opening and said second port is in communication with ambient air; said sensor further connected to the microcontroller and configured to detect a reduction in pressure, and wherein the microcontroller is configured to engage the shape memory alloy actuator when the reduction in pressure is reached, and is configured to engage the housing cap, which is configured to compress the cartridge to deliver medication through the first passage and out of the mouthpiece.

18. The inhalation device of claim 17, wherein said shape memory alloy actuator has a length between 12 and 15 inches, a diameter of 0.015 inches, and wherein heating of the shape memory alloy actuator to its phase change temperature results in a compression of the cartridge of at least 0.055 inches.

* * * * *